United States Patent [19]

Ellis et al.

[11] 4,349,498
[45] Sep. 14, 1982

[54] RADIO-OPAQUE MARKERS FOR PYROLYTIC CARBON PROSTHETIC MEMBERS

[75] Inventors: Willard H. Ellis, Leucadia, Calif.; Axel D. Haubold, Liberty Hill, Tex.; Victor Slivenko, San Diego, Calif.; Jack C. Bokros, Austin, Tex.

[73] Assignee: Carbomedics, Inc., Austin, Tex.

[21] Appl. No.: 225,804

[22] Filed: Jan. 16, 1981

[51] Int. Cl.³ .............................................. A61F 1/22
[52] U.S. Cl. ....................................... 264/81; 427/2; 3/1.5; 3/1; 264/162; 264/219; 264/275; 264/29.5
[58] Field of Search .................. 3/1.5; 264/81, 162, 264/219, 275

[56] References Cited

U.S. PATENT DOCUMENTS

| 3,138,434 | 6/1964 | Diefendorf | 23/209.1 |
| 3,399,969 | 9/1968 | Bokros | 23/209.1 |
| 3,877,080 | 4/1975 | Olcott | 3/1.5 |
| 4,055,861 | 11/1977 | Carpentier | 3/1.5 |
| 4,202,349 | 5/1980 | Jones | 3/1.4 |

*Primary Examiner*—Sam Silverberg
*Attorney, Agent, or Firm*—Fitch, Even, Tabin, Flannery & Welsh

[57] ABSTRACT

Methods are provided for fully encasing radio-opaque markers in pyrocarbon prosthetic members. Inserts having a pyrolytic carbon portion joined to a radio-opaque marker are affixed to a mandrel surface so that the marker extends thereabove. Pyrocarbon sufficient to encase the marker is deposited on the mandrel, the mandrel is removed, and the deposited layer of pyrocarbon is finished to form the prosthetic member.

10 Claims, 22 Drawing Figures

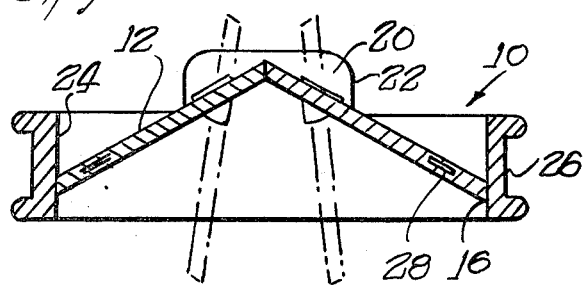
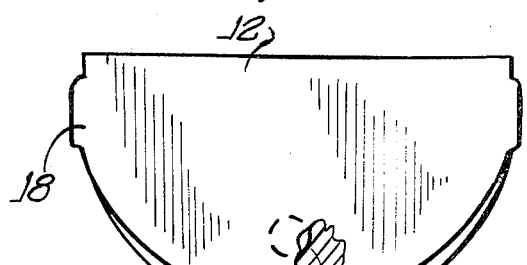
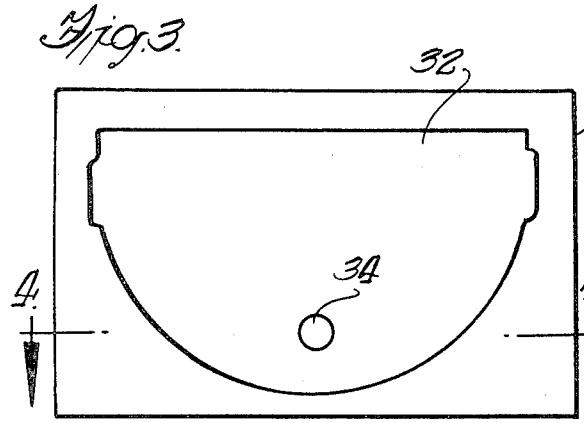
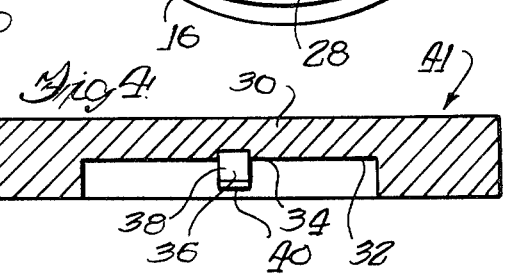
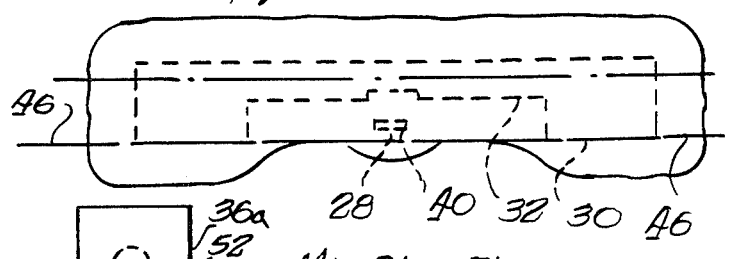
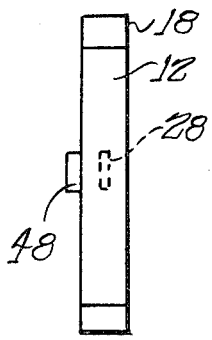
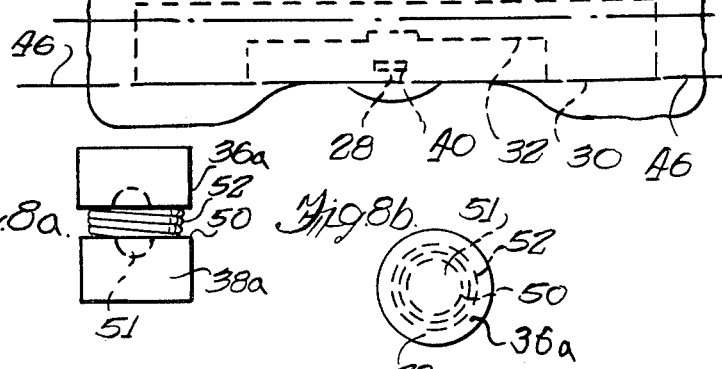
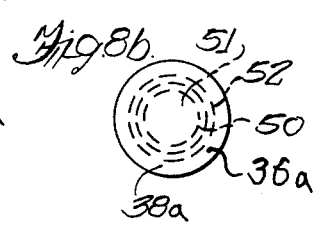
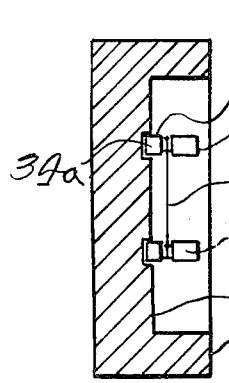
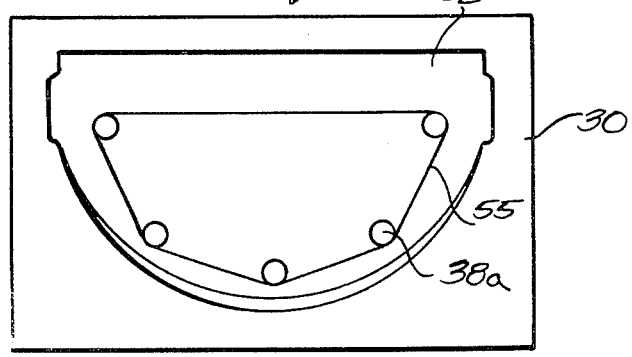

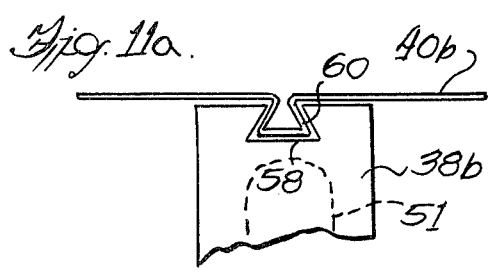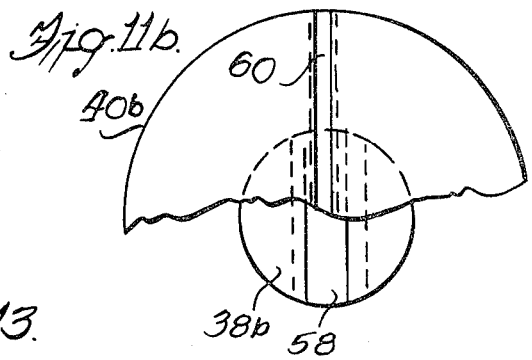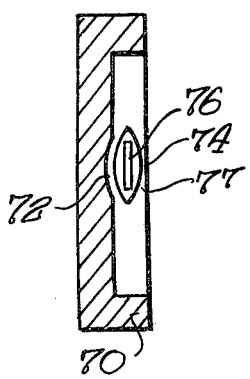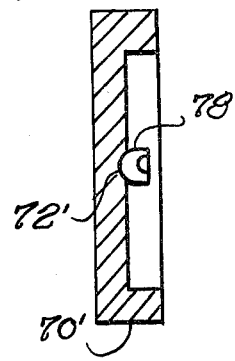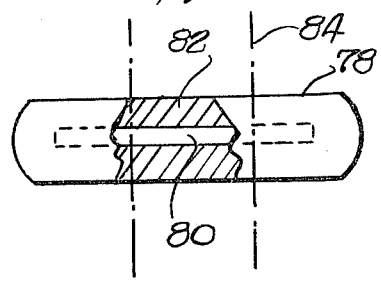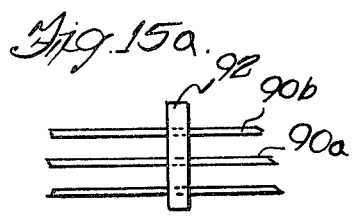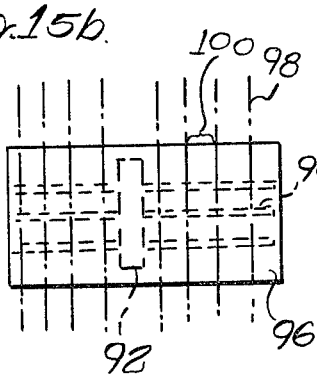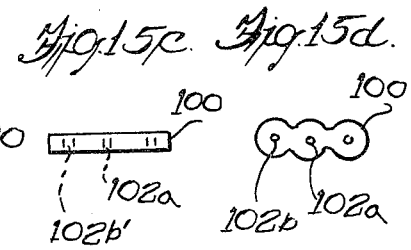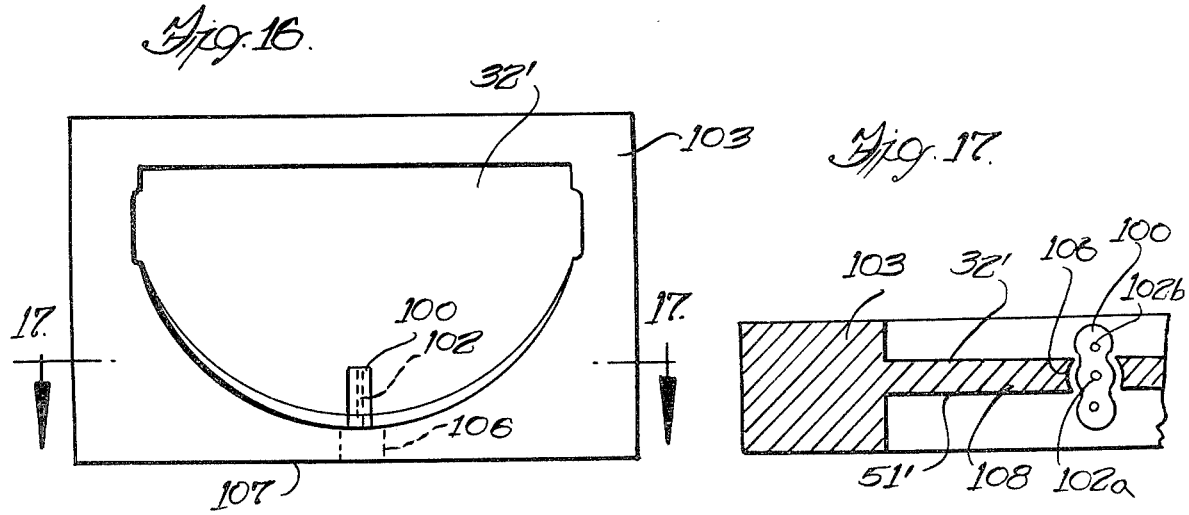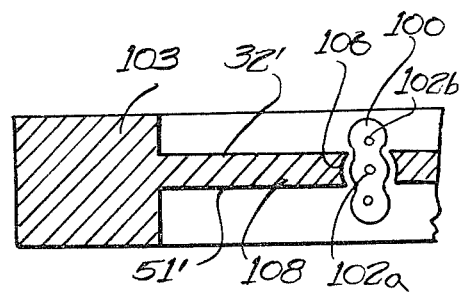

RADIO-OPAQUE MARKERS FOR PYROLYTIC CARBON PROSTHETIC MEMBERS

The present invention related to methods for forming prosthetic devices and more particularly it relates to methods of including radiographic markers in prosthetic device members formed of pyrolytic carbon.

BACKGROUND OF THE INVENTION

Pyrolytic carbon having the characteristics described in U.S. Pat. No. 3,677,795, issued July 18, 1972 to Jack C. Bokros, is particularly suitable for use in prosthetic devices which are implanted in humans and other living animals because it is thromboresistant, having no adverse reaction with blood, and is biocompatable with body tissues so that it does not induce rejection of the implanted device. While in many applications a prosthesis is formed of a suitable substrate material and thereafter coated with pyrolytic carbon, for certain applications, such as to achieve a desired thinness, it may be desirable to form the entire prosthesis or an entire prosthesis member of pyrolytic carbon.

Articles may be formed from a massive deposit of pyrolytic carbon that is created as described in U.S. Pat. No. 3,399,969 issued Sept. 3, 1968, to Jack C. Bokros et al. Exemplary of prosthetic members which may advantageously be formed entirely of pyrolytic carbon are valve members or occluders for heart valves. Pyrolytic carbon provides the thromboresistance and biocompatibility required of heart valve members which are in continuous contact with blood in a critical organ of the body, and pyrolytic carbon has the wear-resistance necessary for continuously moving heart valves which are permanently implanted in the heart. By forming valve members of strong pyrolytic carbon, the valve members may be made very thin yet have the requisite structural strength.

While the importance of manufacturing heart valves to be as mechanically trouble-free as possible cannot be overstated, any mechanical device may not operate forever in its intended fashion, either because of some mechanical difficulty in the heart valve or as a result of changing conditions within the body. From time-to-time, therefore, it may be desirable to monitor an implanted artificial heart valve so as to assure its continuing functioning in the intended manner. Because implantation in the heart precludes direct examination of a heart valve, it would be desirable that the functioning of the valve may be monitored by X-rays.

Because pyrolytic carbon is sufficiently transparent to X-rays so as not to be detectable when implanted in a human body, it would be desirable to include radio-opaque markers in pyrolytic carbon prosthetic members which do not affect their biocompatability when implanted in a human body.

It is an object of the present invention to provide methods of implanting a foreign body in a substantially integral pyrolytic carbon prosthetic member so that the foreign body is fully encased in the member and so that the member has an uninterrupted pyrolytic carbon surface. More specifically, it is an object of the invention to provide a method of forming a prosthetic member of pyrolytic carbon with a radiographic marker fully encased therein.

SUMMARY OF THE INVENTION

A member of a prosthetic device is formed by attaching to a surface of a mandrel, a pyrolytic carbon portion of an insert which supports a radiographic marker. Pyrolytic carbon is deposited on the mandrel to a desired thickness sufficient to fully encase the marker. The mandrel is removed, and the deposited pyrolytic carbon is finished to form the member.

BRIEF DESCRIPTION OF THE DRAWINGS

FIG. 1 is a cross-sectional view of a bileaflet heart valve;

FIG. 2 is an elevation view of a leaflet for the heart valve of FIG. 1;

FIG. 3 is an elevation view of a mandrel for forming the heart valve leaflet shown in FIG. 2;

FIG. 4 is a cross-sectional view of the mandrel taken along line 4—4 of FIG. 3 with a marker-carrying insert received in a cavity;

FIG. 5 is a cross-sectional view of the mandrel-insert assembly which has been coated with pyrolytic carbon;

FIG. 6 is an end elevation view of the carbon layer of FIG. 5 from which excess pyrolytic carbon and graphite have been removed to form a rough leaflet;

FIG. 7 is an end elevation view of the leaflet of FIG. 6 which has been finished by grinding and/or machining;

FIGS. 8a and 8b are, respectively, elevation and plan views of an alternative embodiment of a marker-carrying insert.

FIG. 9 is a cross-sectional view of a heart valve leaflet mandrel having two spaced-apart cavities with inserts received therein and supporting an elongated marker suspended therebetween;

FIG. 10 is an elevation view of a mandrel-insert assembly in which a plurality of pyrolytic carbon plugs support a marker for outlining a leaflet;

FIGS. 11a and 11b are, respectively, elevation and plan views of a further alternative embodiment of a marker-carrying insert;

FIG. 12 is a cross-sectional view of an alternative embodiment of a mandrel having a shallow cavity and having received therein a further alternative embodiment of a marker-carrying insert;

FIG. 13 is a cross-sectional view of the mandrel similar to that of FIG. 12 having a further alternative embodiment of a marker-carrying insert;

FIG. 14 is an enlarged elevation view of a carbon coated wire from which the insert of FIG. 13 is sectioned;

FIGS. 15a–d illustrate the manufacture of inserts for several two-faced mandrels, 15a being an elevation view of a wire assembly, 15b being an elevation view of a pyrolytic carbon coated wire assembly, 15c being an elevation view of an insert formed by sectioning the coated wire segment of FIG. 15b, and FIG. 15d being a plan view of the insert of 15c;

FIG. 16 is an front elevation view of a two-faced mandrel for forming leaflets of the type shown in FIG. 2 containing the insert shown in FIGS. 15c and 15d which has a layer of pyrolytic carbon deposited thereon;

FIG. 17 is a fragmentary cross-sectional view of the mandrel of FIG. 16 containing the insert of FIGS. 15c and 15d.

DETAILED DESCRIPTION OF THE PREFERRED EMBODIMENTS

As an example of a device which may be produced by the methods described herein, a heart valve 10 is illustrated in FIG. 1 which is generally of the type described in U.S. Pat. No. 4,178,639, issued Dec. 18, 1979, to Jack C. Bokros in which a pair of valve members in the form of flat leaflets 12, each having a straight inner edge 14, an arcuate outer edge 16 and ears 18 (FIG. 2) which are pivotably received within depressions 20 in opposed upstanding supports 22, simultaneously pivot to alternately open and close a passageway 24 through the annular valve body 26. While the invention is generally applicable to the manufacture of any pyrolytic carbon prosthetic member having a foreign body fully encased therein, it is particularly applicable to prosthetic members which are movable within the human body such as heart valve members. In accordance with the present invention, heart valve members, such as leaflets 12 are made substantially of pyrolytic carbon, such as that sold under the trademark PYROLITE which has excellant biocompatibility and wear-resistance. A marker 28 (FIG. 2) of a metal or other radio-opaque substance is encased in the pyrolytic carbon to permit X-ray monitoring of the operation of the implanted heart valve 10.

X-ray radiography of living organisms depends upon the differential absorption of X-rays by various members of the organism. Bones, for example, are absorbant, though not completely, of X-rays and are easily distinguishable in X-ray radiography from more transparent soft tissue. Devices formed from carbon are generally transparent to X-rays and are not detectable by X-rays when implanted within a human body. A marker 28, for monitoring by X-rays, should be clearly distinguishable over surrounding background X-ray absorbtion which will include the skeletal structure of the organism. Accordingly, a marker 28, which may necessarily be tiny, should be formed of material which is substantially opaque to X-rays and will generally be metal. Metals which may be used include tantalum, tungsten, molybdenum and rhenium. While certain metals and metal alloys have reasonably good thromboresistance, biocompatibility, and corrosion resistance, pyrolytic carbon has superior thromboresistant and biocompatible qualities to known metals and metal alloys and is a highly preferable choice for surfaces which continually contact blood in critical organs, such as the human heart. Accordingly, the marker 28 is fully encased in the pyrolytic carbon heart valve leaflet 12 so that no surface of the marker is exposed.

A prosthesis member, necessarily or preferably, may be quite thin. Radiographic markers may be included in markers as thin as about 0.1 mm although pyrocarbon members in which radiographic markers may be included may be created which are up to 1 mm thick. Some heart valve members may be less than about 0.3 mm thick. As a part of this invention, a radio-opaque marker is impedded within such a leaflet 12 that is otherwise made entirely of pyrolytic carbon.

Illustrated in FIGS. 3 and 4 is a mandrel 30 having a surface 32 which is substantially the mirror image of a heart valve member 12 to be created thereon by the deposition of pyrolytic carbon. A cavity 34 receives therein an insert 36 which includes a cylindrical pyrolytic carbon plug portion 38 having a metal portion 40 affixed at one end that will serve as the radiographic marker 28 in the manufactured leaflet 12. The metal portion 40 may be in the form of a flat foil disk or a fine wire mesh disc and is mechanically or adhesively affixed to the carbon plug 38. Alternatively, the metal portion 40 may be a film formed by vapor deposition of a radio-opaque metal on the appropriate surface of the carbon plug 38. The carbon plug portion 38 of the insert 36 is inserted in the cavity 34 so that the metal portion 40 projects outward from the mandrel coating surface 32.

The mandrel 30 is most commonly a unitary piece having a surface 32 appropriately machined or otherwise formed for creating the desired device thereon. Since pyrolytic carbon is quite hard and difficult to machine, it is preferred that the surface 32 be substantially a mirror image of at least a portion of the prosthetic member to be formed. The material, of which the mandrel 30 is formed, is selected to withstand the temperature of pyrolytic deposition, i.e. between about 1000° C. and 2300° C., and should have a coefficient of thermal expansion (CTE) within about 50% and preferably between about 5 and 20% more than that of the pyrolytic carbon layer to be formed thereon. A preferred material for the mandrel is polycrystaline graphite, such as that sold under the trademark "POCO graphite". The graphite withstands the temperatures of the pyrolytic carbon coating process and has a thermal coefficient of expansion similar to pyrolytic carbon. Furthermore, the relative softness of such graphite as compared to pyrolytic carbon permits fairly easy machining of the mandrel pursuant to its ultimate removal.

The mandrel-insert assembly 41 (FIG. 4) is coated within a suitable coating chamber. Larger mandrels may be appropriately supported in a coating enclosure, as by thin wires while smaller mandrels may be supported by upwardly flowing gas in a fluidized bed coating chamber. By appropriately adjusting temperature and gas flow rates along with appropriate selection of the hydrocarbon(s) from which the pyrolytic carbon is derived, the desired density, crystallite size, B.A.F. (Bacon Anistropy Factor) and certain strength-related parameters are obtained in the pyrolytic carbon deposited. For structures formed entirely of pyrolytic carbon, the pyrolytic carbon preferably has a density of at least about 1.5 gm/cm$^3$, a B.A.F. of under about 1.3 and an average crystallite size of less than about 200 A.

Pyrolytic carbon, as used herein, is intended to include alloys of pyrolytic carbon formed by codepositing minor portions of other material. It is known, for example, that silicon carbide, in minor amounts, increases the structural strength of pyrolytic carbon without decreasing its biocompatability.

A heart valve leaflet 12 may have a thickness of about 0.7 mm, and a marker 28 may typically have a thickness of about 0.2 mm. For an insert 36, the carbon plug 38 may be proportioned to protrude about 0.2 mm from the mirror image surface 32 of the mandrel 30 so as to position the metal portion 40 of the insert 36 generally midway between the front and back surfaces of the deposited layer. As seen in FIG. 5, pyrolytic carbon coats all surfaces of the mandrel-insert assembly, and coating is continued until a desired thickness of coating 42 is achieved with the metal portion 40 of the insert 36 being surrounded the newly deposited carbon.

The coated assembly may be cut, as along lines 46 of FIG. 5, to trim away excess pyrolytic carbon and portions of the mandrel 30 from the coated substrate. Remaining unwanted portions, usually the entirety, of the graphite mandrel are removed. Relatively soft graphite mandrel material may be removed from the harder pyrolytic carbon by abrasion with a grit of hardness selected to remove the polycrystalline graphite but leave the pyrolytic carbon substantially intact. The abraded leaflet 12 of FIG. 6 may be further machined or ground to remove any remaining excess pyrolytic carbon, such as a protruding portion 48 of the plug 38. Additional machining or grinding may be undertaken to provide beveled edges, polish the surfaces, etc. The leaflet 12 as seen in FIG. 7 is an integral pyrocarbon member with a marker 28 fully encased therein.

The shape of the marker 28 and the positioning of the marker within the carbon leaflet 12 are selected to facilitate fabrication of the leaflet 12 and to be easily observed during radiography. The marker 28 will preferably be positioned at a location for maximum movement within a moving-part prosthesis. In FIG. 2, the marker 28 is positioned toward the apex of the arcuate edge 16 of the leaflet 12 because the apex travels the greatest distance during opening or closing of the valve.

FIGS. 8a and 8b are illustrative of an insert 36a which may be simply constructed. A cylindrical plug 38a has an annular groove 50 in its cylindrical wall. A fine radio-opaque wire 52 is wound a plurality of times within the groove 50 and serves as a marker within the leaflet 12 after pyrocarbon deposition has been completed.

Carbon plugs 38 useful for the present invention may be machined from a block of pyrolytic carbon or may be formed by coating a substrate 51, e.g., a piece of graphite, with pyrolytic carbon under conditions similar to those under which the mandrel 30 will later be coated so that the physical properties of the pyrolytic carbon comprising the plug matches the physical properties of the later-deposited carbon. Thus a substantially complete, homogeneous bond between the plug and the later-deposited carbon will result. After coating the substrate 51, the rough plugs 38 are lightly machined to form the grooves 50 and finish the edges. It is necessary that the substrate 51 of the inserted plug 38 be completely above the deposit surface 32 of the mandrel 30 so that the substrate is not exposed in the finished prosthetic member.

In FIG. 9, two spaced-apart carbon plug portions 38a support an elongated radio-opaque marker 54 therebetween. The plugs 38a are of the type illustrated in FIGS. 8a and 8b having annular grooves 50 in which a metal wire or metal ribbon is wound. The plugs 38a are inserted in spaced-apart cavities 34a and a metal wire or metal ribbon is wound around the grooves so as to suspend the wire or ribbon between the plugs and provide an elongated marker 54. This concept may be expanded, as shown in FIG. 10, by stringing a wire 55 between a plurality of grooved plugs 38a to outline the periphery of the leaflet to be formed.

FIGS. 11a and 11b are exemplary of a further method by which a radio-opaque metal portion 40b may be affixed to a carbon plug 38b. A dovetail slot 58 is provided in the exposed end of a cylindrical plug 38b, and a cooperating dovetail fold 60 of a disk-shaped metal item 40b may be slidably inserted in the slot. More simply, a thin foil metal item 40b may simply be pressed into the dovetail slot 58 to affix the metal item 40b to the plug 38b.

As another alternative method of affixing an insert to a mandrel, an adhesive may be used to secure the pyrocarbon portion of the insert to the mandrel. Illustrated in FIGS. 12 and 13 are mandrels 70 and 70' having shallow cavities 72 and 72' in which inserts are adhesively bonded. The adhesive must maintain its bonding properties through the extremely high temperatures of pyrolytic coating. Graphite cement is particularly suitable for this purpose. In FIG. 12 the insert 74 is comprised of a foil disk 76 encased in a shell 77 of pyrolytic carbon. Two inserts 78 of the type that is used in FIG. 13 are formed by coating a wire segment 80 (FIG. 14) with pyrolytic carbon and cutting the coated wire segment 82 along lines 84 perpendicular to the axis of the wire. The resulting end sections are used as inserts 78 which are adhesively affixed by their carbon coated end in the shallow cavity 72', and the center section is discarded.

An efficient method of manufacturing markers containing inserts for a number of prosthetic members is illustrated in FIGS. 15a–d. Three wires 90 are supported in parallel alignment by a common support 92. The three wire assembly is coated with sufficient pyrolytic carbon so that the coating bridges the space between adjacent wires 90. Although only segments of the outer wires 90b are to serve as radio-opaque markers, the coated center wire 90a completes the continuous pyrocarbon web between the wire and thereby supports the segments of the outer wires. The coated structure 96 (FIG. 15b) may be cut along lines 98 perpendicular to the wire axes to form insert segments 100 (FIGS. 15c and 15d) having three spaced wire segments 102 in a pyrolytic carbon web. The outside segments 102b are used to provide radio-opaque markers for two prosthetic members in a bisurface mandrel such as that illustrated in FIGS. 16 and 17 which has two deposit surfaces 32' along which two leaflets 12, of the type illustrated in FIG. 2, are created by pyrolytic deposition of carbon. A hole 106 is drilled into the mandrel 103 from one side 107 and opens to the deposit surfaces 32' on both sides of the thin wall 108 therebetween. The insert 100 of FIG. 15c is inserted in the hole 106. The center wire segment 102a fits snugly into the hole 106 between the deposit surfaces 51', and the side wire segments 102b extend exterior of the surfaces 32'. From the coating deposited on the mandrel 103, two leaflets 12 may be obtained, each having one of the side wire segments 102b encased therein. In the process of cutting away the mandrel 103 to separate the leaflets 12, the center wire segment 102a is cut away and discarded.

Heart valves having pyrolytic carbon leaflets containing radio-opaque markers are designed for surgical implantation in the heart. While such heart valves are carefully manufactured for trouble-free, life-long use, various factors may cause a mechanical device, such as a heart valve, to malfunction. Because of the difficulties and dangers associated with open-heart surgery, it is to be hoped that an artificial heart valve will never have to be replaced, and the use of radio-opaque markers will permit the monitoring of such a valve. One potential problem would be the incomplete opening of or closing of the leaflets. X-ray monitoring should reveal that the marker is not moving the intended distance, indicating that the valve is not fully opening and closing. In a bi-leaflet or multi-leaflet valve, X-ray monitoring may reveal that one of the leaflets responds to pressure change slower than the other(s) indicating sticking.

EXAMPLE

A mandrel having a cylindrical mirror image surface in the shape of a heart valve leaflet is formed by machining a block of POCO graphite. A cavity with a maximum depth of 0.2 mm is formed into the negative surface on which the leaflet is to be created.

Discs of tungsten foil 0.2 mm thick and 1.0 mm in diameter are placed in a pyrolytic coating chamber and levitated therein by a fluidized bed of upwardly flowing helium at 1350° C. Thereafter, propane is introduced to the flow of helium so that the gas mixture has a partial pressure of about 0.4 atmosphere propane and about 0.6 atmosphere helium. Coating is continued for about 45 minutes at 1350° C. with a gas flow rate of 20 liters per minute (STP), until the discs are encased in a shell of pyrolytic carbon approximately 0.8 mm thick. The pyrolytic carbon has a B.A.F. of about 1.2, a density of about 1.7 gm/cc and an average crystallite size of about 50 A.

Graphite cement is applied to the surface of the cavity of the mandrel, and one of the pyrocarbon-coated discs is placed therein. After the adhesive is set, the mandrel, to which the insert is adhered, is suspended by wires in the coating chamber and coated under conditions substantially identical to those under which the foil discs are coated. Coating continues for a period of 1.5 hours until a layer of pyrolytic carbon about 0.8 mm thick covers the surfaces of the mandrel and surrounds the insert.

After allowing the coated mandrel to cool, excess pyrolytic carbon is cut away, and the remaining mandrel portion is removed by blasting the mandrel portion with a suitable grit, such as sodium bicarbonate, which has a hardness substantially less than pyrocarbon.

The newly deposited pyrolytic carbon has substantially the same parameters as the pyrolytic coating on the disc. A metallographic section is taken through the coated interface between the plug and the freshly deposited pyrolytic coating and examined metallographically. The examination reveals that substantially complete bonding is achieved between the plug and the later deposit of pyrocarbon.

While the entire invention has been described in terms of certain preferred embodiments, modifications obvious to one with ordinary skill in the art may be made without departing from the teachings of the invention. For example, the invention is applicable to prostheses other than heart valves including non-moving prosthesis members. A dental implant for supporting an artificial tooth may be made of pyrolytic carbon wherein a radio opaque marker is fully encased in a pyrolytic carbon root portion so that the position of the root portion may be monitored by X-ray during and after implantation.

The method of the invention may be used to encase other types of foreign bodies in pyrolytic carbon. For research purposes, one way wish, for example, to implant a radioactive marker in a prosthesis and insert the prosthesis in a laboratory animal.

Various features of the invention are set forth in the following claims.

What is claimed is:

1. A method of forming a pyrolytic carbon prosthetic member having a marker fully encased in pyrolytic carbon comprising;
    forming a mandrel having a surface on which the member is to be created,
    providing an insert having a pyrolytic carbon portion and a marker joined thereto,
    affixing said insert to said mandrel so that said marker extends above said surface, and
    depositing pyrolytic carbon on said mandrel to a desired thickness sufficient to fully encase said marker therein,
    removing undesired portions of said mandrel, and
    finishing the shaping of said deposited pyrolytic carbon to form a prosthetic member.

2. A method according to claim 1 wherein said marker is radio-opaque.

3. A method according to claim 1 wherein said marker is vapor deposited on a surface of said carbon portion.

4. A method according to claim 1 wherein said prosthetic member is a heart valve member.

5. A method according to claim 1 including providing a cavity in said mandrel surface and securing said carbon portion of said insert in said cavity.

6. A method according to claim 1 wherein said insert is formed by depositing pyrolytic carbon on said marker.

7. A method according to claim 1 wherein said surface is substantially the mirror image of at least a portion of said prosthetic member.

8. A method of forming a pyrolytic carbon prosthetic member having an elongated marker fully encased in pyrocarbon comprising;
    forming a mandrel having a surface on which the member is to be created,
    affixing spaced-apart pyrocarbon plugs to said mandrel so that portions thereof extend above said surface,
    supporting an elongated marker between said plugs,
    depositing pyrolytic carbon on said mandrel to a desired thickness sufficient to fully encase said marker therein,
    removing unwanted portions of said mandrel, and
    finishing the shaping of said deposited pyrolytic carbon to form a prosthetic member.

9. A method according to claim 8 including removing a portion of said pyrolytic carbon plugs as a part of said finish shaping.

10. A method according to claim 8 wherein said surface is substantially the mirror image of at least a portion of said prosthetic member.

* * * * *